(12) United States Patent
Ekstam

(10) Patent No.: US 10,398,866 B1
(45) Date of Patent: Sep. 3, 2019

(54) SYSTEM AND METHOD FOR SECURING AN AIRWAY DEVICE IN A STATIONARY POSITION

(71) Applicant: Christopher L. Ekstam, Colleyville, TX (US)

(72) Inventor: Christopher L. Ekstam, Colleyville, TX (US)

(*) Notice: Subject to any disclaimer, the term of this patent is extended or adjusted under 35 U.S.C. 154(b) by 438 days.

(21) Appl. No.: 15/245,351

(22) Filed: Aug. 24, 2016

Related U.S. Application Data

(60) Provisional application No. 62/209,104, filed on Aug. 24, 2015.

(51) Int. Cl.
*A61M 16/04* (2006.01)

(52) U.S. Cl.
CPC .............. *A61M 16/0497* (2013.01)

(58) Field of Classification Search
CPC ........ A44B 18/0084; A61B 2050/0065; A61B 50/30; A61C 5/90; A61M 16/04; A61M 16/0447; A61M 16/0461; A61M 16/0463; A61M 16/0465; A61M 16/0488; A61M 16/0493; A61M 16/0497; A61M 16/0666; A61M 16/0683; A61M 16/0688; A61M 16/0875; A61M 2025/0206; A61M 2025/0213; A61M 2025/022; A61M 2025/0226; A61M 2025/024; A61M 2025/0246; A61M 2025/0253; A61M 2025/026; A61M 2025/0266; A61M 2025/0273; A61M 2205/0205; A61M 2205/0238; A61M 2207/00; A61M 2209/06; A61M 2209/088; A61M 2210/0618; A61M 2210/0625; A61M 2230/005; A61M 2240/00; A61M 25/02; F16L 3/08; Y10S 128/15; Y10S 128/24; Y10S 128/26; Y10S 128/911; Y10S 128/912; Y10S 24/11; Y10S 602/903; Y10T 24/1318; Y10T 24/14; Y10T 24/207; Y10T 24/33; Y10T 29/49826
See application file for complete search history.

(56) References Cited

U.S. PATENT DOCUMENTS 3,834,380 A * 9/1974 Boyd .................... A61M 25/02
                                                                    128/DIG. 26
3,924,636 A * 12/1975 Addison ........... A61M 16/0488
                                                                    128/206.25

(Continued)

*Primary Examiner* — Annette Dixon
(74) *Attorney, Agent, or Firm* — Eldredge Law Firm, LLC; Richard Eldredge

(57) ABSTRACT

An apparatus to secure an airway tube within a mouth of a user and in a fixed position relative to a user's head. The apparatus includes a support structure having a vertical member rigidly attached to and extending perpendicular to a horizontal member; a first strap having a front surface fixedly secured to the vertical member and a back surface configured to removably engage with the airway tube; a second elongated strap having a first section and a second section; a first locking device secured to the front surface of the first strap and configured to secure the first strap in a wrapped position around the airway tube; and a second locking device secured at an end of the first section of the second strap and configured to secure the first section to the second section.

3 Claims, 7 Drawing Sheets

(56) References Cited

U.S. PATENT DOCUMENTS

| | | | | |
|---|---|---|---|---|
| 4,142,527 | A | * | 3/1979 | Garcia ................ A61M 25/02 128/DIG. 26 |
| 4,449,527 | A | * | 5/1984 | Hinton ............... A61M 16/0488 128/207.17 |
| 5,205,832 | A | * | 4/1993 | Tuman ............... A61M 16/0488 128/912 |
| 5,341,802 | A | * | 8/1994 | Calebaugh ........ A61M 16/0488 128/207.17 |
| 5,868,132 | A | * | 2/1999 | Winthrop .......... A61M 16/0488 128/207.14 |
| 8,096,300 | B2 | * | 1/2012 | Russo ............... A61M 16/0488 128/202.27 |
| 2006/0118120 | A1 | * | 6/2006 | Russo ............... A61M 16/0488 128/207.14 |
| 2009/0211573 | A1 | * | 8/2009 | Russo ............... A61M 16/0488 128/200.26 |

* cited by examiner

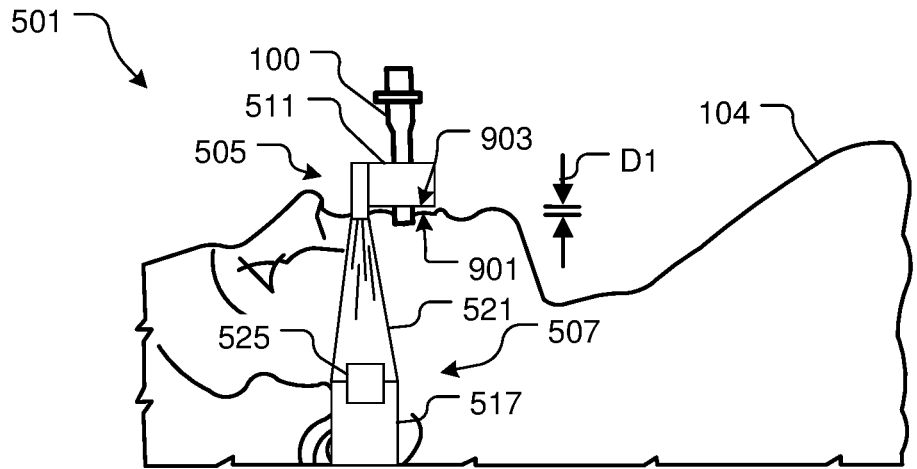

FIG. 9

| | |
|---|---|
| 1003 | Securing a locking mechanism to the tube of the airway device with a first strap, second strap, and an adhesive |
| 1005 | Securing the locking mechanism at height relative to the lips of the patient with a support structure |
| 1007 | Securing the support structure in a stationary position with a head harness |
| 1009 | Securing the head harness to the face with an adhesive strip and wrapping the head harness to the head with a first and second strap |

FIG. 10

SYSTEM AND METHOD FOR SECURING AN AIRWAY DEVICE IN A STATIONARY POSITION

BACKGROUND

1. Field of the Invention

The present invention relates generally to systems and methods to secure an airway device in a stationary position.

2. Description of Related Art

Systems and methods to secure an airway device 102 in a stationary position are well known in the art. In FIG. 1, a simplified side view of an airway device 102 includes a tube 100 that extends through the mouth 103 of the patient 104, through the air passage 105 and communicates with the patient's lung 107. In FIG. 2, a conventional device 101 is shown having two strips of tape 200, 203 having adhesive surfaces and configured to engage with both the tube 100 and the face of the patient to retain the tube 100 in a stationary position.

A common problem associated with device 101 is that the adhesive strips can cause damage to the sensitive lips and face after time. Further, it is common for the doctor to reuse the adhesive strips, which in turn could transfer germs to different parties. Accordingly, there has been a long-felt need for a new device configured to secure the tube in a stationary position without these problems.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 9 is a side view of the system of FIG. 5;

FIG. 10 is a flowchart depicting the preferred method of use; and

Figure 1:
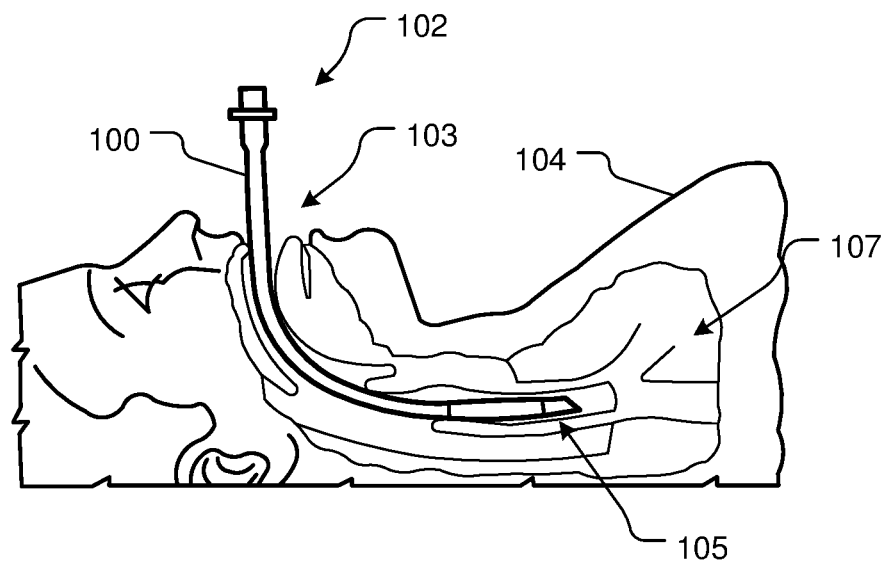
FIGS. 1 and 2 are simplified side views of a conventional device to secure an airway tube in a stationary position.
Figure 2:
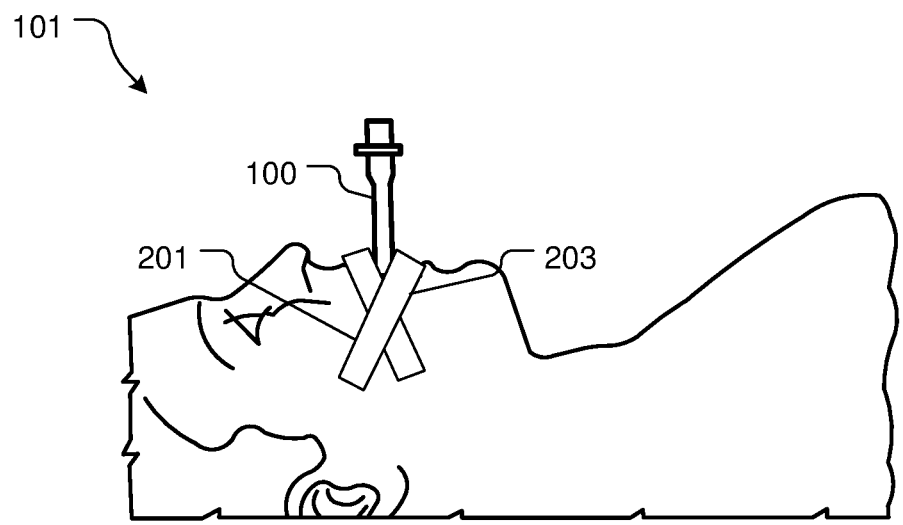

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional airway support devices. Specifically, the system and method of the present application provides rapid and effective means to support the tube of the airway device without coming in contact with the lips and mouth of the patient. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 3:
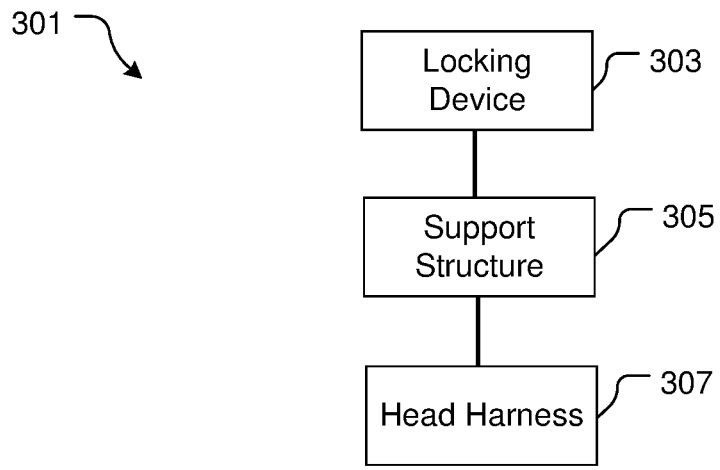
FIG. 3 is a simplified schematic of a preferred system and method to secure an airway tube of an airway device in a stationary position.

Referring now to the drawings wherein like reference characters identify corresponding or similar elements throughout the several views, FIG. 3 depicts a simplified schematic of an airway device support system 301 in accordance with a preferred embodiment of the present application. It will be appreciated that system 201 overcomes one of more of the above-listed problems commonly associated with the conventional support devices.

In the contemplated embodiment, system 201 includes one or more of a locking device 303 configured to engage with the tube of the airway device, a support structure 305 fixedly secured to the locking device 303 and configured to secure the locking device 303 at a distance relative to the lips and mouth of the patient, and a head harness 307 fixedly secured to the support structure 305 and configured to engage with the head of the patient.

It will appreciated that the components of system 301 provides effective means to secure the tube of the airway device in a stationary position while positioned within the patient. The system 301 also provides means to secure the locking device at a distance, which in turn reduces the discomfort to the patient during and after the procedure. Further, the system 301 is composed of material that allows easy disposal after use.

Figure 4:
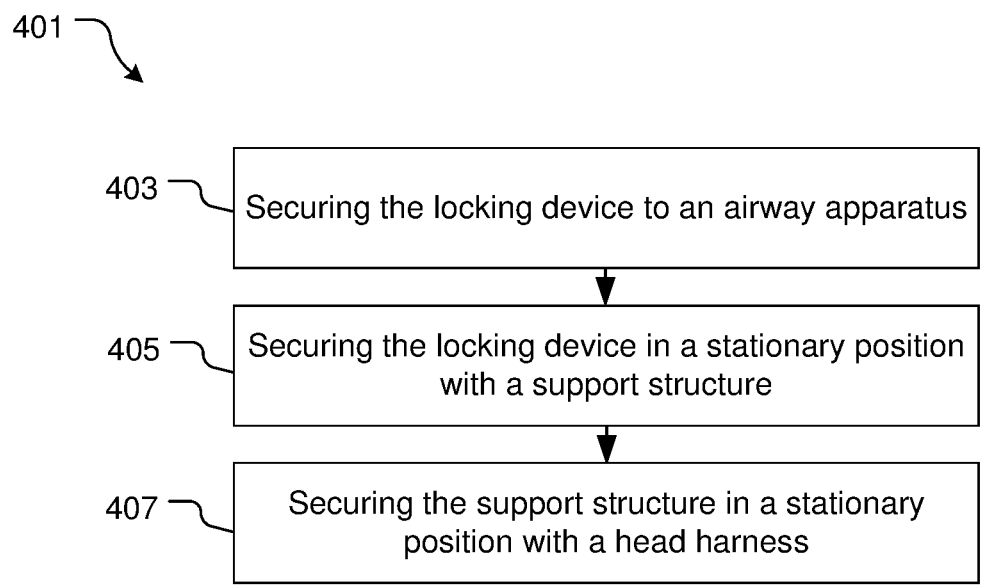
FIG. 4 is a flowchart depicting the preferred process.

Referring now to FIG. 4, one preferred process is shown in flowchart 401, which includes securing the locking device to the airway device, securing the locking device in a stationary position with the support structure, and securing the support structure in a stationary position with a head harness; the process being depicted in boxes 403, 405, and 407.

Figure 5:
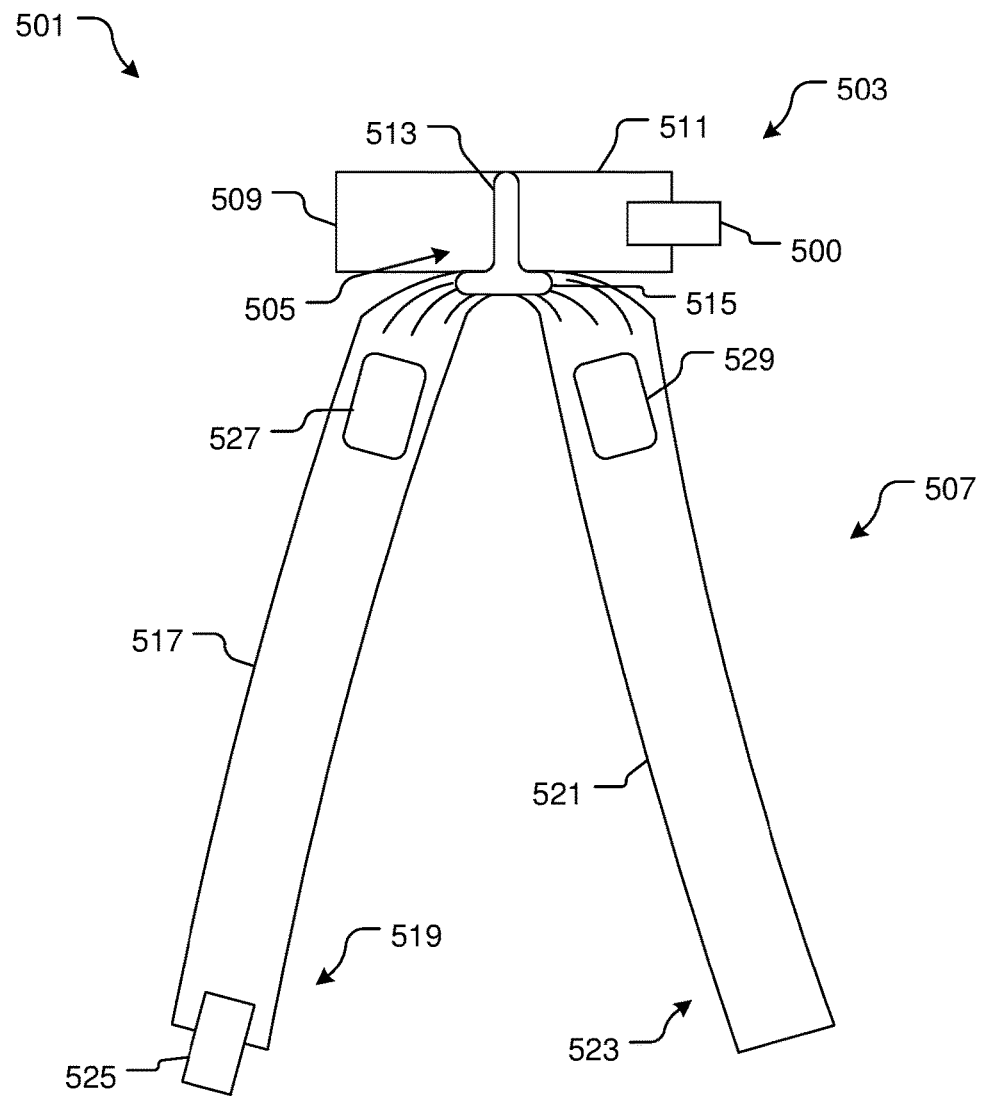
FIG. 5 is a rear view of a system of FIG. 3.
Figure 6:
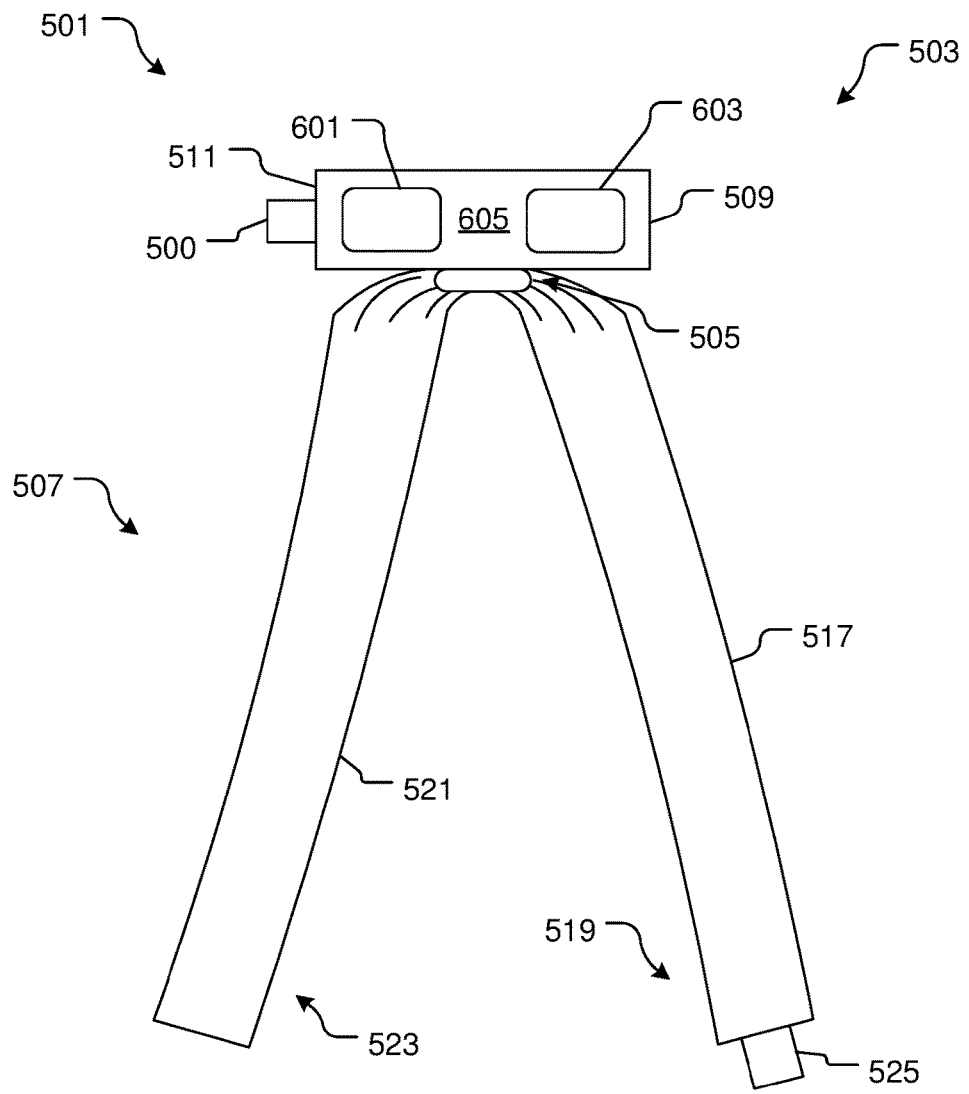
FIG. 6 is a front view of the system of FIG. 5.

In FIGS. 5 and 6, one of the preferred embodiments of system 301 is shown. A rear view of system 501 is depicted having a locking device 503, a support structure 505, and a head harness 507.

In the exemplary embodiment, locking device 503 includes a first strap 509 integral with a second strap 511 and having a middle section 701 (see, e.g., FIG. 7) joining the first and second straps together and configured to fixedly engage with a vertical member 513 of support structure 505.

Figure 7:
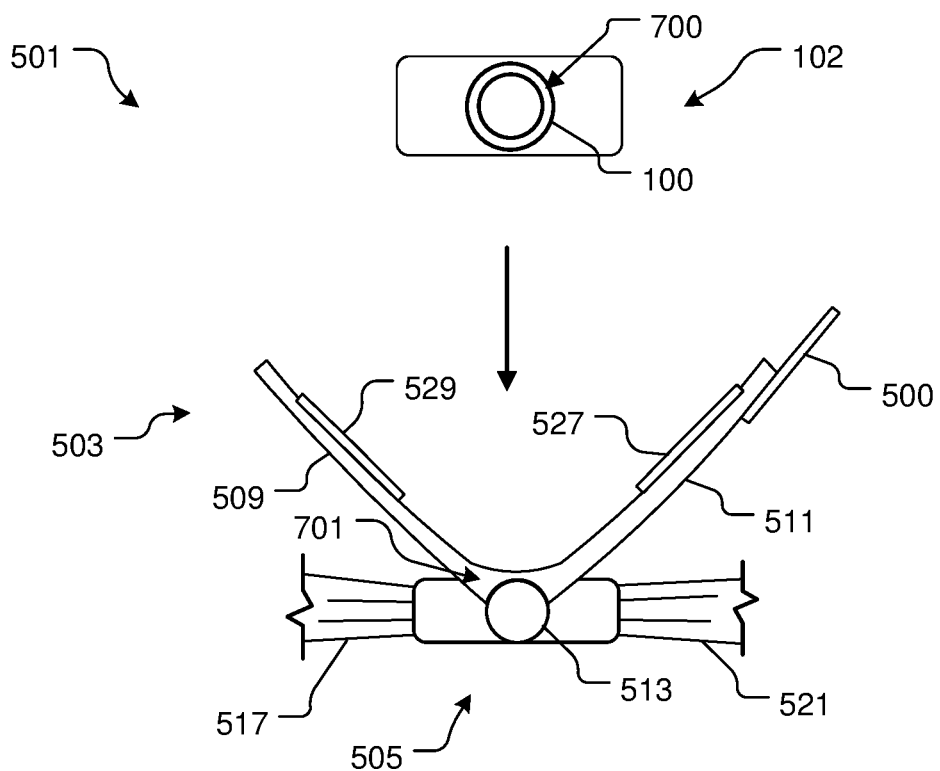
FIGS. 7 and 8 are top views of the system of FIG. 5.
Figure 8:
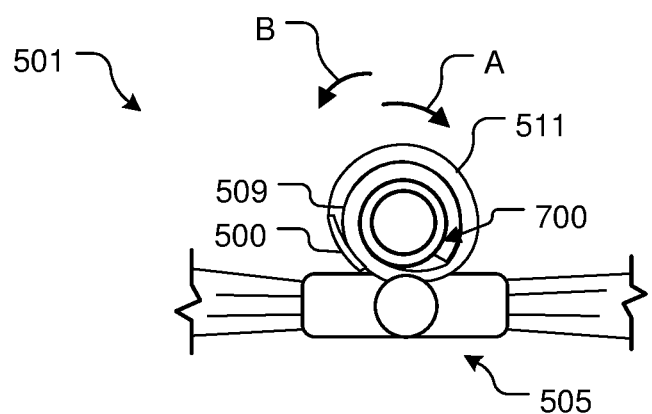

During use, the locking device 503 is configured to engage with the tube 100 of airway device 102, as shown in FIGS. 7 and 8. Although shown as having two straps, it will be appreciated that it is also contemplated having alternative embodiments that include other forms of locking mechanisms configured to engage with the tube. Such embodiments could include clips, clamps, other forms of quick-release device, and the like.

Support structure 505 includes a vertical member 513 integrally joined to a horizontal member 515, which in turn engages with the head harness 507. In the preferred embodiment, the support structure 505 is composed of a rigid material configured to elevate the locking device 503 at a height relative to the face of the patients such that the locking device does not come into contact with the lips and/or mouth of the patient. In one embodiment, the support structure 505 could be composed of a disposable elastomeric material.

In the contemplated embodiment, locking device 503 is an adhesive strip; however, it should be known that it is also contemplated using different types of locking devices, including hook-loop fasteners, clips, snaps, buttons, and the like. In these embodiments, the straps could include two members, e.g., male and female members of a snap, on each end and configured to engage with each other. It will be appreciated that having an adhesive device and/or hook-loop fastener allows selective adjustment around the head of the patient.

Figure 11:
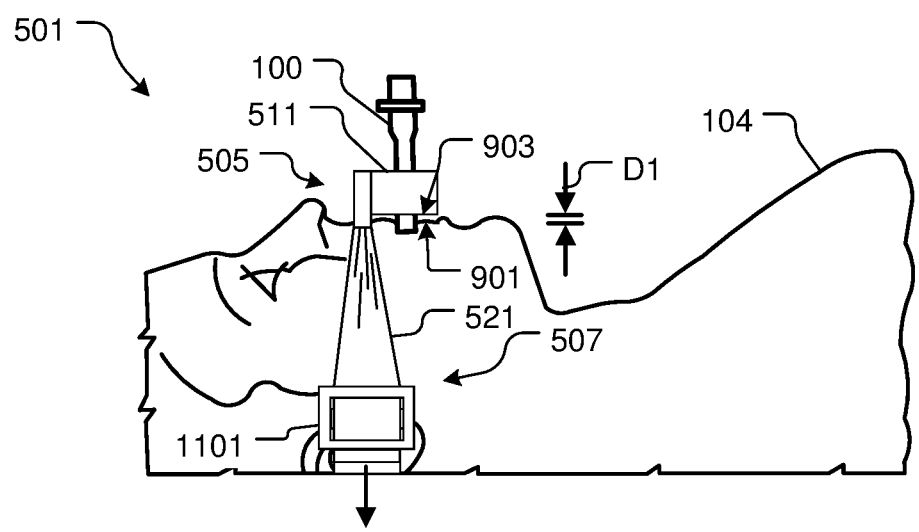
FIG. 11 is an alternative embodiment of the system of the present application.

The head harness 507 includes a first strap 517 have an end 519 and a second strap 521 integral with the first strap 517 and having an end 523. During use, the first and second straps are configured to extend around the periphery of the head of the patient and configured to retain the support structure in a stationary position. To achieve this feature, it is contemplated having a locking device 525 at end 519 and configured to engage with a surface of strap 521, as shown in FIG. 9. In another embodiment, it is contemplated having a buckle 1101 secured to strap 517 and configured to engage with strap 521, as shown in FIG. 11. During use, the strap 521 is adjusted in length relative to strap 517 via buckle 1101 to create a tight fit around the head of the patient. In one embodiment, the straps 517, 521 are composed of an elastic material, which allows selective reach and adjustment around the head of the patient.

It is contemplated having two adhesive strips 527, 529 on the surfaces of respective straps 517, 521. In this embodiments, the adhesive strips could be utilized for additional stationary support by securing the straps directly to the face between the nose, lips, and partially on the cheeks of the patient. It will be appreciated that the adhesive strips 527, 529 are optional features of the present system.

Referring specifically to FIG. 6, a front view of system 501 is shown. In the exemplary embodiment, locking device 501 includes two adhesive strips 601, 603 secured to surface 605 and configured to engage with the outer periphery of the tube 100 for additional support and rigidity.

Top views of system 501 are shown in FIGS. 7 and 8 and illustrates the process of securing the locking device 503 to the outer surface 700 of tube 100 via straps 509, 511, as depicted with arrows "A" and "B." After wrapped around the surface 700, the straps are secured in position with an adhesive strip 500. The adhesive strips 527, 529 come into contact and secure to surface 700 during this process.

As shown in the side view of FIG. 9, the system 501 provides effective means to secure the tube 100 in a stationary position at a height D1 relative to surface 901, e.g., the lips, of the patients. The height D1 is the distance between a bottom surface 903 of straps 509, 511 and surface 901 of the patient 104.

In FIG. 10, a flowchart 1001 is shown depicting one preferred method of use for system 501, which includes the process of securing a locking mechanism to the tube of the airway device with a first strap, second strap, and an adhesive; securing the locking mechanism at height relative to the lips of the patient with a support structure; securing the support structure in a stationary position with a head harness; and securing the head harness to the face with an adhesive strip and wrapping the head harness to the head with a first and second strap; the process being depicted in boxes 1003, 1005, 1007, and 1009.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An apparatus for securing an airway tube within a mouth of a user and in a fixed position relative to a user's head, comprising:
   a support structure, having:
      a first member attached to a second member in a rigidly perpendicular relationship;
   a first strap, having:
      a front surface fixedly secured to the first member; and
      a back surface configured to removably engage with the airway tube;
   a second elongated strap having:
      a first section and a second section, and
      a first adhesive strip secured to the first section and a second adhesive strip secured to the second section, the first adhesive strip and the second adhesive strip are configured to engage with a face of the user for added stability;
   wherein a middle area disposed between the first section and the second section is fixedly secured to the second member, wherein the first section and the second section are configured to wrap around a periphery of a head of the user; and wherein the first strap and the second elongated strap extend perpendicular to each other;

a first locking device secured to the front surface of the first strap and configured to secure the first strap in a wrapped position around the airway tube; and a second locking device secured at an end of the first section of the second elongated strap and configured to secure the first section to the second section;

wherein the first member is integrally joined to the second member;

wherein the support structure is composed of rigid material configured to elevate the first locking device at a height relative to a face of the user such that the first locking device does not come into contact with a lip and/or a mouth of the user; and wherein the first strap and the second elongated strap are composed of an elastic material, which allows selective reach and adjustment around the user's head.

2. The apparatus of claim 1, further comprising:

an adhesive strip secured to the back surface of the first strap and configured to removably engage with the airway tube.

3. The apparatus of claim 1, wherein the second locking device is a buckle.

* * * * *